(12) United States Patent
Oronsky et al.

(10) Patent No.: US 8,138,169 B2
(45) Date of Patent: Mar. 20, 2012

(54) COMBINATION THERAPY FOR BIPOLAR DISORDER

(75) Inventors: Bryan T. Oronsky, Los Altos Hills, CA (US); Neil C. Oronsky, Los Altos Hills, CA (US)

(73) Assignee: ComgenRx, Inc., Mountain View, CA (US)

( * ) Notice: Subject to any disclaimer, the term of this patent is extended or adjusted under 35 U.S.C. 154(b) by 424 days.

(21) Appl. No.: 12/422,156

(22) Filed: Apr. 10, 2009

(65) Prior Publication Data

US 2009/0311347 A1 Dec. 17, 2009

Related U.S. Application Data

(60) Provisional application No. 61/050,738, filed on May 6, 2008, provisional application No. 61/044,312, filed on Apr. 11, 2008.

(51) Int. Cl.
*A61K 31/485* (2006.01)
*A61K 31/496* (2006.01)
*A61K 31/53* (2006.01)
*A61K 31/554* (2006.01)

(52) U.S. Cl. .............. 514/211.13; 514/242; 514/254.04; 514/282

(58) Field of Classification Search ............. 514/211.13, 514/242, 254.04, 282
See application file for complete search history.

(56) References Cited

U.S. PATENT DOCUMENTS

| | | | |
|---|---|---|---|
| 4,952,402 A | 8/1990 | Sparks et al. |
| 5,500,227 A | 3/1996 | Oshlack et al. |
| 5,900,420 A | 5/1999 | Cole |
| 5,945,416 A | 8/1999 | Shannon et al. |
| 5,972,932 A | 10/1999 | Benvenga et al. |
| 6,294,195 B1 | 9/2001 | Oshlack et al. |
| 6,455,536 B1 | 9/2002 | Brotchie |
| 6,608,088 B1 | 8/2003 | Nicolodi et al. |
| 6,716,449 B2 | 4/2004 | Oshlack et al. |
| 6,740,659 B2 | 5/2004 | Brotchie |
| 6,863,901 B2 | 3/2005 | Hirsh et al. |
| 7,201,920 B2 | 4/2007 | Kumar et al. |
| 2007/0213394 A1 | 9/2007 | Beguin et al. |

FOREIGN PATENT DOCUMENTS

WO  WO-2008066916 A1  6/2008

OTHER PUBLICATIONS

Boothby et al. Buprenorphine for the treatment of opioid dependence. American Journal of Health-System Pharamcy, 2007, 64 (3), pp. 266-272, abstract.*
Brown, et al., "Naltrexone in Patients with Bipolar Disorder and Alcohol Dependence," Depression and Anxiety, 2006, vol. 23, No. 8, pp. 492-495.
Carlezon, et al., "Kappa-Opioid Ligands in the Study and Treatment of Mood Disorders," Pharmacology and Therapeutics, XP002548302, Sep. 2009, vol. 123, No. 3, pp. 334-343.
International Search Report and Written Opinion mailed on Jan. 25, 2010, for PCT Application No. PCT/US2009/040272, 17 pages.
Kamin, et al., "Extrapyramidal Side Effects in the Psychiatric Emergency Service," Psychiatric Service, Mar. 2000, vol. 51, No. 3, pp. 287-289.
Levin, et al., "Bipolar Disorder and Substance abuse," Biological Psychiatry, XP004649079, vol. 56, No. 10, Nov. 2004, pp. 738-748.
Magura, et al., "Outcomes of buprenorphine Maintenance in Office-Based Practice," Journal of Addictive Diseases, vol. 26, No. 2, Jan. 2007, pp. 13-23.
Murphy, et al., "The Effects of Pentazocine, a Kappa Agonist, in Mania," Neuropsychopharmacology, XP009123535, vol. 31, No. Suppl. 1, Dec. 2006, pp. 243-247.
Schaffer, et al., "Mood-Elevating Effects of Opioid Analgesics in Patients with Bipolar Disorder," Journal Neurophsychiatry. vol. 19, No. 4, 2007, pp. 449-452.
Tomasiewicz, et al., "The Kappa-Opioid agonist U69.593 Blocks Cocaine-Induced Enhancement of Brain Stimulation Reward," XP002548303, Dec. 2008, vol. 64, pp. 982-988.

* cited by examiner

*Primary Examiner* — Jennifer M Kim
(74) *Attorney, Agent, or Firm* — Goodwin Procter LLP

(57) ABSTRACT

Treatment regimens for mood disorders that include administration of buprenorphine, alone or in combination with additional pharmacological agents are described. Specifically, treatment regimens that alleviate racing thoughts associated with bipolar disorder, and pharmaceutical compositions and kits for use therein are described. Dosing regimens, compositions, and kits including buprenorphine for treating mania associated with opioid withdrawal are also described.

16 Claims, No Drawings

COMBINATION THERAPY FOR BIPOLAR DISORDER

CROSS-REFERENCE TO RELATED APPLICATIONS

This application claims priority to U.S. Provisional Patent Application Ser. No. 61/044,312 filed on Apr. 11, 2008 and U.S. Provisional Patent Application Ser. No. 61/050,738 filed on May 6, 2008, each of which is hereby incorporated by reference in its entirety.

FIELD

Treatment regimens for mood disorders that include administration of buprenorphine, alone or in combination with additional pharmacological agents are described. Specifically, treatment regimens that alleviate racing thoughts associated with bipolar disorder, and pharmaceutical compositions and kits for use therein are described. The buprenorphine and other pharmacological agents can be administered at therapeutic or subtherapeutic doses to treat the racing thoughts. Dosing regimens, compositions, and kits including buprenorphine for treating mania associated with opioid withdrawal are also described.

BACKGROUND

Bipolar disorder, also known as manic-depressive illness, is a disorder that causes unusual shifts in a individual's mood, energy, and ability to function. Different from the normal ups and downs that people experience, the symptoms of bipolar disorder are generally severe. They can result in damaged relationships, poor job or school performance, and even suicide.

Bipolar disorder typically develops in late adolescence or early adulthood. However, some people have their first symptoms during childhood, and some develop them late in life. Bipolar disorder is a long-term illness that usually requires management throughout an individual's life.

Bipolar disorder typically causes dramatic mood swings, from overly elated ("high") and/or irritable to sad and hopeless, and then back again, often with periods of normal mood in between. Severe changes in energy and behavior oftentimes are experienced with these changes in mood. The periods of highs and lows are referred to as episodes of mania and depression.

Signs and symptoms of mania (or a manic episode) may include the following: increased energy, activity, and restlessness; excessively "high," overly good, euphoric mood; extreme irritability; racing thoughts and talking very fast, jumping from one idea to another; distractibility (e.g., difficulty concentrating); decreased need for sleep; unrealistic belief in one's abilities and powers; poor judgment; spending sprees; a lasting period of behavior that is different from usual; increased sexual drive; abuse of drugs (particularly cocaine, alcohol, and sleeping medications); and provocative, intrusive, or aggressive behavior. A manic episode may be diagnosed if elevated mood occurs with three or more of the other symptoms most of the day, nearly every day, for one week or longer.

Signs and symptoms of depression (or a depressive episode) may include the following: lasting sad, anxious, or empty mood; feelings of hopelessness or pessimism; feelings of guilt, worthlessness, or helplessness; loss of interest or pleasure in activities once enjoyed; decreased energy, a feeling of fatigue or of being "slowed down"; difficulty concentrating, remembering, or making decisions; restlessness or irritability; sleeping too much, or difficulty sleeping; change in appetite and/or unintended weight loss or gain; chronic pain or other persistent bodily symptoms that are not caused by physical illness or injury; and thoughts of death or suicide, or suicide attempts. A depressive episode may be diagnosed if five or more of these symptoms last most of the day, nearly every day, for a period of two weeks or longer.

A mild to moderate level of mania is generally referred to as hypomania. Hypomania may feel good to the individual who experiences it and may even be associated with good functioning and enhanced productivity. Thus, even when family and friends learn to recognize the mood swings as possible bipolar disorder, the individual may deny that anything is wrong. Without proper treatment, however, hypomania can become severe mania or can switch into depression.

Sometimes severe episodes of mania or depression include symptoms of psychosis. Common psychotic symptoms are hallucinations (hearing, seeing, or otherwise sensing the presence of things not actually there) and delusions (false, strongly held beliefs not influenced by logical reasoning or explained by an individual's usual cultural concepts). Psychotic symptoms in bipolar disorder tend to reflect the extreme mood state at the time. For example, delusions of grandiosity, such as believing one is the President or has special powers or wealth, may occur during mania; delusions of guilt or worthlessness, such as believing that one is ruined and penniless or has committed some terrible crime, may appear during depression.

It may be helpful to think of the various mood states in bipolar disorder as a spectrum or continuous range. At one end is severe depression, above which is moderate depression and then mild low mood, which many people call "the blues" when it is short-lived but is termed "dysthymia" when it is chronic. Then there is normal or balanced mood, above which comes hypomania (mild to moderate mania), and then severe mania.

In some people, however, symptoms of mania and depression may occur together in what is called a mixed bipolar state. Symptoms of a mixed state often include agitation, trouble sleeping, a significant change in appetite, psychosis, and suicidal thinking. An individual may have a very sad, hopeless mood while at the same time feeling extremely energized.

Bipolar disorder may also initially present as a problem other than mental illness. For instance, it may surface as alcohol or drug abuse, poor school or work performance, or strained interpersonal relationships. Such problems in fact may be signs of an underlying bipolar disorder.

The classic form of the illness, which involves recurrent episodes of mania and depression, is called bipolar I disorder. Some individuals, however, never develop severe mania but instead experience milder episodes of hypomania that alternate with depression; this form of the illness is called bipolar II disorder. When four or more episodes of illness occur within a 12-month period, an individual is said to have rapid-cycling bipolar disorder. Some individuals experience multiple episodes within a single week, or even within a single day.

Bipolar disorder may be treated with medication and psychosocial therapy. For example, medications known as mood stabilizers may be prescribed. In general, individuals with bipolar disorder continue treatment with mood stabilizers for years. Other medications may be added when necessary, typically for shorter periods, to treat episodes of mania or depression that break through despite the mood stabilizer.

However, despite the use of mood stabilizers, drugs, e.g., alcohol, prescription drugs, or other illicit drugs, are often used as a form of "self-medication" in order to counteract unpleasant psychological symptoms (such as racing thoughts), which often leads to abuse of these drugs. Patients with bipolar disorder and other psychiatric disorders may also demonstrate somatization and therefore seek out "pain management" doctors, because the analgesics, hypnotics and stimulants commonly prescribed in this context can help to temporarily relieve or control dysphoric symptoms experienced in part as physical pain.

The high rates of drug abuse amongst patients with psychiatric disorders has been documented. See, e.g., Cerullo and Strakowski, *Subst Abuse Treat Prev Policy* (2007) 2:29. For example, Cerullo and Strakowski report that the lifetime history of any drug abuse or dependence is 84% for antisocial personality disorder, 62% for bipolar disorder types I and II, and 47% for schizophrenia, compared with 27.2% for major depressive disorder and 17% for the general population.

However, drug abuse, e.g., opioid abuse, and opioid withdrawal, can actually worsen mood symptoms and significantly complicate the course and prognosis of bipolar disorder or any other psychiatric illness, resulting in increased suffering, disability, and costs through more frequent and prolonged affective episodes, decreased compliance with treatment, a lower quality of life, and increased suicidal behavior.

Accordingly, new regimens for treating unpleasant and/or difficult to treat symptoms of psychiatric disorders, especially bipolar disorder would be useful. Treatment regimens that address drug abuse and withdrawal, e.g., opioid abuse and withdrawal, would also be useful. In particular, treatment regimens that are provided as kits would be desirable.

SUMMARY

Described here are treatment regimens and compositions and kits for use therein that may be beneficial in stabilizing mood, increasing medication compliance, and preventing drug abuse in subjects with bipolar disorder. The treatment regimens may achieve mood stabilization by administering a partial opioid agonist, e.g., buprenorphine, in a predetermined fashion. For example, when a plurality of buprenorphine doses are administered per day, the first dose may be higher than any additional dose given. In one variation, a morning dose of buprenorphine, e.g., a dose administered at 6 am, may be higher than a buprenorphine dose given in the evening, e.g., a dose administered at 6 pm, or in the late evening, e.g., at 12 am (midnight). The first dose of buprenorphine may range from about 1.0 mg to about 32 mg. For example, the first dose may be about 1.0 mg, about 2.0 mg, about 4.0 mg, about 8.0 mg, about 16 mg, about 24 mg, or about 32 mg of buprenorphine. The lower dose of administered buprenorphine may range from about 0 mg to about 4.0 mg. For example, the first administered dose may be about 0 mg, about 0.5 mg, about 1.0 mg, about 2.0 mg, or about 4.0 mg. It is understood that any suitable number of doses may be administered. For example, one dose, two doses, three doses, or four doses may be administered. In some variations, the treatment regimens may include rapidly decreasing the buprenorphine dose over the course of a day. In other variations, a gradual decrease in the buprenorphine dose is employed (over a day).

The treatment regimens may be useful in treating mania associated with opioid withdrawal. Here it is the belief of the inventors that when a higher dose of buprenorphine is taken in the evening or late evening (e.g., to treat opioid withdrawal), it acts as a mood destabilizer and thus, kindles mania or mania-like symptoms in this patient population. In another variation, the treatment regimens may be beneficial in alleviating racing thoughts during the depressive phase of bipolar disorder. The treatment regimens may further include one or more active agents (supplemental agents), for treating comorbid conditions associated with bipolar disorder.

As used herein, a "manic episode" is defined by criteria set forth in the DSM-IV (Diagnostic and Statistical Manual of Mental Disorders, Fourth Edition, 2000, American Psychiatric Association, Washington, D.C), which is hereby incorporated herein by reference for all purposes, as a distinct period of abnormally and persistently elevated, expansive, or irritable mood, lasting at least one week wherein three (or more) of the following symptoms have persisted and have been present to a significant degree:

(1) inflated self-esteem or grandiosity
 (2) decreased need for sleep (e.g., feels rested after only 3 hours of sleep)
 (3) more talkative than usual or pressure to keep talking
 (4) flight of ideas or subjective experience that thoughts are racing
 (5) distractibility (i.e., attention too easily drawn to unimportant or irrelevant external stimuli)
 (6) increase in goal-directed activity (either socially, at work or school, or sexually) or psychomotor agitation
 (7) excessive involvement in pleasurable activities that have a high potential for painful consequences (e.g., engaging in unrestrained buying sprees, sexual indiscretions, or foolish business investments)

The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

A "mixed episode" is observed when criteria are met both for a manic episode (see above) and for a major depressive episode, as defined in the DSM-IV, nearly every day during at least a one week period and the mood disturbance is sufficiently severe to cause marked impairment in occupational functioning or in usual social activities or relationships with others, or to necessitate hospitalization to prevent harm to self or others, or there are psychotic features. As with a manic episode, the symptoms are not due to the direct physiological effects of a substance (e.g., a drug of abuse, a medication, or other treatment) or a general medical condition (e.g., hyperthyroidism).

A "hypomanic episode" is defined by the DSM-IV as a distinct period of persistently elevated, expansive, or irritable mood, lasting throughout at least four days, that is clearly different from the usual nondepressed mood. During the period of mood disturbance, three (or more) of the symptoms listed above for "manic episode" above, have persisted and have been present to a significant degree. The episode is associated with an unequivocal change in functioning that is uncharacteristic of the individual when not symptomatic. The disturbance in mood and the change in functioning are observable by others. The episode is not severe enough to cause marked impairment in social or occupational functioning, or to necessitate hospitalization, and there are no psychotic features. The symptoms are not due to the direct physiological effects of a substance (e.g., a drug of abuse, a medication, or other treatment) or a general medical condition (e.g., hyperthyroidism).

As used herein, the phrase "opioid withdrawal" refers to a variety of signs and complaints appearing with the abrupt removal of, or a rapid decrease in the regular dosage of opioids. The symptoms stop when an opioid agonist is taken again. Physical manifestations may include sweating, nausea, yawning, chills, diarrhea, papillary dilation, piloerection, tachycardia, increased blood pressure, hypersensitivity to pain, stomach cramps, and muscle cramps. Psychological manifestations of opioid withdrawal observed may include dysphoria, restlessness, irritability, anxiety, and depression. Onset often begins within 6-24 hours from last opioid use.

The terms "treating" or "alleviating" interchangeably refer to delaying the onset of, retarding or reversing the progress of, or preventing either the disease or condition to which the term applies, or one or more symptoms of such disease or condition.

The term "patient," "subject," or "individual" interchangeably refer to a mammal, for example, a domesticated mammal (canine or feline), a laboratory mammal (murine, rattus, lagomorpha), or a human.

A variation of the methods described here includes treating mania associated with opioid withdrawal in a subject by administering a first dose of a kappa opioid and at least one additional dose of the kappa opioid to the subject according to a predetermined dosage regimen, where the at least one additional dose is less than the first dose. The first dose may be administered in the morning, e.g., at 6 am or between about 6 am and 9 am, and the at least one additional dose may be administered in the afternoon, e.g., at 12 pm (noon) or between about 12 pm and 3 pm, evening, e.g., at 6 pm or between about 6 pm and 9 pm, or late evening, e.g., at 12 am (midnight). The kappa opioid may be a kappa receptor antagonist including, but not limited to, 5'-guanidinonaltrindole, buprenorphine, norbinaltorphimine, JDTic, and combinations thereof. In one variation, the kappa receptor antagonist is buprenorphine. The buprenorphine may be administered in doses of about 0.5 mg, about 1.0 mg, about 2.0 mg, about 8.0 mg, about 16 mg, about 24 mg, about 32 mg, or combinations thereof. In some variations, a subtherapeutic dose of buprenorphine is administered.

By "subtherapeutic dose" it is meant a dose of a kappa opioid, e.g., buprenorphine, either as an administered dose of the kappa opioid, or actual level of the kappa opioid in a subject that functionally is insufficient to elicit the intended pharmacological effect in itself (e.g., analgesia, pain relief, reversal of opioid withdrawal symptoms, reduction of psychotic symptoms, prevention of epileptic seizure, etc.), or that quantitatively is less than the established therapeutic dose for that particular kappa opioid (e.g., as published in a reference consulted by a individual of skill, for example, doses for a pharmacological agent published in the Physicians' Desk Reference, $62^{nd}$ Ed., 2008, Thomson Healthcare or Brunton, et al., Goodman & Gilman's The Pharmacological Basis of Therapeutics, $11^{th}$ edition, 2006, McGraw-Hill Professional). A "subtherapeutic dose" can be defined in relative terms (i.e., as a percentage amount (less than 100%) of the amount of the kappa opioid conventionally administered). For example, a subtherapeutic dose amount can be about 1% to about 75% of the amount of kappa opioid conventionally administered. In some variations, a subtherapeutic dose can be about 10%, 20%, 25%, 30%, 50% or 75% of the amount of kappa opioid conventionally administered.

In another variation, the kappa opioid may be a kappa receptor agonist including, but not limited to, butorphanol, BRL-52537, cyclazocine, enadoline, GR-89696, HZ-2, ICI-204,448, ketazocine, LPK-26 (2-(3,4-Dichlorophenyl)-N-methyl-N-[(1S)-1-(2-isopropyl)-2-(1-(3-pyrrolinyl))ethyl] acetamide), nalbuphine, pentazocine, salvinorin A, spiradoline, tifluadom, U-50488, U-62066, U-69593, and combinations thereof.

The predetermined dosing regimens may administer the first dose of the kappa opioid in the morning and at least one additional dose of the kappa opioid in the evening. In one variation, two or more additional doses of the kappa opioid are administered in a gradually decreasing fashion.

In other variations, a second active agent may be administered to help with mood stabilization. Exemplary second active agents include without limitation, antipsychotic agents, atypical antipsychotic agents, antiepileptic agents, lithium, P-450 CYP3A4 inhibitors, P-450 CYP2D6 inhibitors, CB1 agonists, CB2 agonists or antagonists, salts, and acids thereof, and combinations thereof. When atypical antipsychotics are employed, they may include without limitation, aripriprazole, arisulpride (amisulpride), olanzapine, paliperidone, quetiapine, risperidone, ziprasidone, and combinations thereof. The predetermined dosing regimens may be designed so that the second active agent is administered in the morning or the evening. In some variations, the second active agent is administered multiple times a day. The second active agent may also be administered in a rapidly or gradually increasing or decreasing manner throughout the day. In some variations, the second active agent is administered in an increasing manner, i.e., the morning dose is lower than the evening or late evening dose. In other variations, the dosing of the second active agent and partial opioid agonist is inverse to one another. In yet further variations, the second active agent may be administered so that the highest dose is in the evening and the lowest dose is in the morning.

Further active agents (supplemental agents) may be administered to treat comorbid conditions associated with bipolar disorder, a side-effect of the second active agent, or another symptom associated with bipolar disorder. The comorbid condition may be a sleep disorder. Exemplary sleep disorders include without limitation, hypoventilation-obesity syndrome (Picwickian syndrome), idiopathic hypersomnia, narcolepsy, night terrors, parasomnias, primary snoring, sleep apnea, nocturnal sleep-related eating disorder, spousal arousal syndrome, upper airway resistance syndrome, and combinations thereof. In some variations, the sleep disorder may be due to alcoholism, allergic rhinitis, altered light-dark cycles, amphetamine use, antidepressant use, anxiety, asthma, benzodiazepine withdrawal, chronic fatigue syndrome, chronic obstructive pulmonary disease (COPD), chronic pain, cocaine use, compulsive hyperphagia, anorexia, bulimia, anorexia-bulimia, starvation, restricted caloric intake, dementia, disturbances in circadian rhythm, dyspnea, edema, eneuresis, fibromyalgia, food intolerance, gastroesophageal reflux, hyperammonemia, hypersensitivity to stimulants, incontinence, infection, inflammatory bowel syndrome, irritable bowel syndrome, modafinil (Provigil® tablet) use, neuromuscular disorders, nocturia, nocturnal myoclonus, orthopnea, paroxysmal nocturnal dyspnea, pica, Prinzmetal's angina, pruritis, racing thoughts, restless leg syndrome, seizure disorder, sinusitis, sleepwalking, or combinations thereof.

Other comorbid conditions include diabetes mellitus, obesity, and fibromyalgia. An exemplary side-effect of the second active agent may be an extrapyrimidal symptom such as akisthesia.

The kappa opioids, second active agents, and supplemental agents may be provided in any suitable dosage form. For example, the dosage forms may be liquid, solid, or semi-solid. They may also be formulated for any suitable mode of administration, such as, but not limited to, oral, sublingual, buccal, parenteral, intravenous, intramuscular, subcutaneous, topical, inhalation, and needle-free administration. In some variations, the first dose and the at least one additional dose of the kappa opioid are provided in the same dosage form. In other variations, the first dose and the at least one additional dose of the kappa opioid are provided in different dosage forms. Exemplary dosage forms include without limitation, powders, granules, capsules, films, transdermal patches, buccal patches, sublingual formulations, gums, chewables, oral strips, rapid dissolve tablets, coated tablets, solutions, ointments, creams, and gels. In some instances, the composition comprises a sublingual formulation within a rapid dissolve tablet. In other instances, the composition comprises a sublingual formulation surrounded by a buccal patch. In yet further instances, the composition comprises a sublingual formulation surrounded by a mouth strip. It is understood that other composition forms are also contemplated.

In some variations, the kappa opioids, e.g., buprenorphine, second active agents, and supplemental agents are provided in separate dosage forms and co-administered (administered in combination) with each other, e.g., taken at the same time or sequentially. In other variations, the kappa opioids, e.g., buprenorphine, second active agents, and supplemental agents are co-formulated together, i.e., they are included in a single dosage form.

The compositions for use with the methods described herein may include a partial opioid agonist, e.g., a kappa-receptor antagonist such as buprenorphine, and a second active agent in a single dosage form, where the second active agent comprises an antipsychotic agent, an atypical antipsychotic agent, an antiepileptic agent, lithium, naloxone, a P-450 CYP3A4 inhibitor, a P-450 CYP2D6 inhibitor, salts and acids thereof, and combinations thereof. The single dosage form may be a powder, granules, capsules, films, transdermal patches, buccal patches, sublingual formulations, gums, chewables, oral strips, rapid dissolve tablets, coated tablets, solutions, ointments, creams, and gels. In one variation, the single dosage form comprises a sublingual formulation within a rapid dissolve tablet. In some variations, the second active agent includes an atypical antipsychotic. For example, the atypical antipsychotic may include aripriprazole, arisulpride, olanzapine, paliperidone, quetiapine, risperidone, ziprasidone, or combinations thereof.

Kits for treating mania associated with opioid withdrawal that include a plurality of buprenorphine dosage forms and instructions for administering the dosage forms according to a predetermined dosage regimen are also described. Here the predetermined dosing regimen may include administering a first buprenorphine dose and at least one additional buprenorphine dose that is less than the first dose. The predetermined dosing regimen may provide that the first dose be administered in the morning, e.g., at 6 am or between about 6 am and 9 am, and the at least one additional dose administered in the afternoon, e.g., at 12 pm (noon) or between about 12 pm and 3 pm, evening, e.g., at 6 pm or between about 6 pm and 9 pm, or late evening, e.g., at 12 am (midnight).

The kits may include a housing configured to organize the dosage forms according to the predetermined dosing regimen. For example, the housing may be configured to organize the plurality of dosage forms into morning dosage forms and evening dosage forms. In some variations, the housing may be configured to organize the plurality of buprenorphine dosage forms according to a rapidly or a gradually decreasing dosing regimen. In yet further variations, the housing may be configured to organize the buprenorphine dosage forms according to the day of the week to be taken.

The kits may also include a second dosage form having one or more second active agents. The second active agent may also help to stabilize the mood of the patient. Exemplary second active agents include without limitation, aripriprazole, arisulpride, olanzapine, paliperidone, quetiapine, risperidone, ziprasidone, and combinations thereof. The kit may further include additional dosage forms that include one or more additional agents for treating a comorbid condition. For example, an antihistamine may be useful to include when the comorbid condition is a sleep disorder. Dosage forms that include other active agents (e.g., to treat comorbidities) or second active agents (e.g., for mood stabilization) may be organized in the housing similar to the organization provided for the buprenorphine dosage forms, as described above.

Also described here are methods for treating a bipolar condition/disorder and subtypes thereof in a subject experiencing racing thoughts by administering buprenorphine to the subject to alleviate the racing thoughts. Subtypes of a bipolar condition may include without limitation, bipolar I disorder, bipolar II disorder, mixed bipolar disorder, rapid-cycling bipolar disorder, hypomania, cyclothymia, acute mania, drug-induced mania, or drug-induced hypomania. The methods may be applicable to racing thoughts experienced during a depressive episode (instead of during the manic phase). In some variations, an opioid antagonist is also administered. In other variations, a second active agent is administered to the subject to help stabilize their mood. Such agents may include antipsychotic agents, atypical antipsychotic agents, antiepileptic agents, lithium, and salts and acids thereof, and combinations thereof. Supplemental or additional agents may also be administered to treat a comorbid condition, a side-effect of the second active agent, a symptom associated with the bipolar condition, or combinations thereof. In other instances, light therapy may be used to treat the racing thoughts, other symptoms associated with the bipolar disorder, a comorbid condition, or a side-effect of the second active agent.

The kits for treating the symptom of racing thoughts in bipolar disorder may include a plurality of buprenorphine dosage forms, at least one second dosage form comprising a second active agent that helps to stabilize mood, e.g., an atypical antipsychotic agent, and instructions for taking the dosage forms according to a predetermined dosing regimen. Dosage forms including an opioid antagonist such as naloxone may also be included. In some variations, dosage forms having a supplemental or additional agent for treating a comorbid condition, side-effect of second agent, and/or other symptoms of bipolar disorder may be provided in the kits.

The kits may further include a housing configured to organize the dosage forms according to the predetermined dosing regimen. For example, the housing may be configured to organize the plurality of dosage forms into morning dosage forms and evening dosage forms. In some variations, the housing may be configured to organize the plurality of dosage forms according to a rapidly or a gradually decreasing dosing regimen. In yet further variations, the housing may be configured to organize the dosage forms according to the day of the week to be taken. The kits may also be tailored to treat particular bipolar conditions or subtypes. For example, the kits may be tailored to treat bipolar I disorder, bipolar II disorder, mixed bipolar disorders, rapidly-cycling bipolar disorder, acute mania, drug-induced mania, hypomania, cyclothymia, or combinations thereof.

DETAILED DESCRIPTION

Described herein are treatment regimens and compositions and kits for use therein that may be beneficial in stabilizing mood, increasing medication compliance, and preventing drug abuse in subjects with bipolar disorder. As previously stated, the treatment regimens may achieve mood stabilization by administering a partial opioid agonist, e.g., a kappa-receptor antagonist such as buprenorphine, in a predetermined fashion. The amount and frequency of administration of the partial opioid agonist will vary depending on such factors as the particular type of bipolar disorder diagnosed, associated symptoms and/or comorbidities, other medications being taken by the patient, and previous history of opioid abuse. For example, when a plurality of buprenorphine doses are administered per day, the first dose may be higher than any additional dose given. In some variations, a morning dose of buprenorphine may be higher than a buprenorphine dose given in the evening or late evening. For example, a buprenorphine dose administered at 6 am may be higher than a buprenorphine dose given in the evening, e.g., at 6 pm, or late evening, e.g., at 12 am (midnight). In some variations, the treatment regimens may include rapidly decreasing the buprenorphine dose over the course of a day. In other variations, a gradual decrease in the buprenorphine dose is employed (over a day).

The treatment regimens may be useful in treating mania associated with opioid withdrawal. This may be due to the destabilizing effect of buprenorphine when taken in the evening by patients undergoing opioid withdrawal treatment. As previously stated, it is the belief of the inventors that when higher doses of buprenorphine are taken in the evening, it acts as a mood destabilizer and thus, kindles mania or mania-like symptoms in this patient population. In another variation, the treatment regimens may be beneficial in alleviating racing thoughts during the depressive phase of bipolar disorder.

A variety of studies have implicated buprenorphine in the induction of mania or manic episodes. See, e.g., Jagadheesan and Muirhead, *Aust NZ J Psychiatry* (2004) 38(7):560; Leza, et al., *Gen Pharmacol* (1991) 22(2):293-6; and Robertson and Taylor, *J Feline Med. Surg.* (2004) 6(5):321-33. However, contrary to the published literature, the inventors have found that kappa opioids such as buprenorphine, either administered alone or in combination with other active agents, is efficacious in mood stabilization when a lower dose is administered in the evening, and also efficacious in alleviating racing thoughts associated with the depressed phase(s) of bipolar disorder. Accordingly, buprenorphine may be useful in treating mania associated with opioid withdrawal. The inventors have also found that buprenorphine administration may improve patient compliance with prescribed medication regimes by better stabilizing their bipolar symptoms, and in some instances, may improve compliance by reducing the number of medications needed to effectively treat bipolar disorder symptoms.

For example, bipolar disorder patients are prone to narcotic abuse because when initially taken, the narcotics elevate their mood. However, when the narcotic wears off, the patients become even more depressed, resulting in a desire to take more narcotics, which then wear off, etc., resulting in an oscillating behavioral pattern that negatively effects the course of their bipolar disorder. For instance, patients with co-occurring substance use may have more prolonged affective episodes and may generally be less compliant with treatment. In some cases, more mood stabilizer needs to be prescribed to help control symptoms. Contrastingly, the inventors have found that bipolar disorder patients being administered buprenorphine according to the dosing regimens described herein may be less likely to take other narcotic substances. Given that buprenorphine administration has been found to alleviate symptoms such as anxiety, irritability, and racing thoughts, patients on buprenorphine therapy may be less predisposed to self-medicate with benzodiazepines. They may also be less likely to take antidepressants to alleviate depressive symptoms. This is also beneficial because antidepressants have been associated with triggering mama.

Compliance may also be reduced due to the detrimental side-effects that may be experienced with conventional bipolar disorder treatments. Currently, mania is treated with mood stabilizers and antipsychotic medications. Both classes of medications are accompanied with potentially harmful side effects. Lithium, used as a mood stabilizer, can produce sometimes significant weight gain, acne with scarring, thinning of hair, and pronounced tremor. Administration of antipsychotic medications can result in the development of extrapyramidal symptoms (EPS) consisting of extreme motor restlessness (akathisia), prolonged muscle contraction (dystonia), parkinsonism and repetitive, involuntary purposeless movements such as grimacing, blinking, lip smacking, puckering and pursing (tardive dyskinesia) which have a significant impact on tolerability and adherence in addition to impacting function. The use of antipsychotics has also been associated with neuroleptic malignant syndrome, a life threatening neurological disorder. These side effects render compliance difficult. This may be especially true for individuals with co-occurring substance abuse; a significant proportion of individuals suffering from mania and/or bipolar disorder.

Compliance may also be affected by sleep disturbance. Sleep problems in bipolar disorder are universal and persistent; they represent both a symptom of the condition and a cause. Bipolars tend to exhibit impaired sleep efficiency, higher levels of anxiety and fear about poor sleep, and a tendency to misperceive that the sleep they are getting is inadequate. See, e.g., Harvey et al., *Am J Psychiatry* 162:50-57, January 2005. The underlying cause of their anxiety is often awareness that sleep loss can herald or intensify periods of manic or hypomanic activity. This anxiety may then serve to perpetuate the insomnia which in turn exacerbates the disease. The prevalence of opioid and benzodiazepine abuse is partially explainable in terms of the effectiveness of these drugs on promoting sleep. Medicines other than full opioid agonists and benzodiazepines which promote sleep may therefore have a particularly palliative effect in this population both as abortive therapy during a manic or hypomanic episode and as prophylactic therapy to prevent an episode.

I. Compositions

The compositions described here for mood stabilization may include any suitable active agent in any pharmaceutically acceptable form. For example, the compositions may include any pharmaceutically acceptable salts, prodrugs, racemic mixtures, conformational and/or optical isomers, crystalline polymorphs and isotopic variants of the active agents. The compositions may also be configured to have any suitable form, e.g., solid, semi-solid, or liquid. The compositions may also be provided in unit dose form. In general, the compositions may include a partial opioid receptor agonist, e.g., a kappa-receptor agonist or a kappa-receptor antagonist, and one or more additional active agents. The compositions may also be configured to include any suitable type of release kinetics. For instance, the compositions may be configured to release the partial opioid agonist, or one or more active agents in a controlled release, delayed release, sustained release, immediate release, pulsatile, or continuous manner.

Partial Opioid Agonists

The compositions described here may include any suitable partial opioid agonist. The partial opioid agonists will generally be compounds having some agonist activity at opioid receptors. However, because they are weak agonists, they may also function as opioid receptor antagonists. Partial opioid agonists that may be useful here include buprenorphine, thienorphine, pentazocine, propiram, lofexidine, nalorphine, butorphanol and oxilorphan. Partial opioid agonists are also generally reviewed in Chapter 21, section III of Goodman and Gilman's *The Pharmacological Basis of Therapeutics*, supra, which is incorporated herein by reference. The partial opioid agonist may be a kappa opioid, i.e., a compound having activity at the kappa ($\kappa$) opioid receptor. In one variation, the kappa opioid is a kappa receptor agonist. In another variation, the kappa opioid is a kappa receptor antagonist, e.g., buprenorphine.

Buprenorphine is 17-(cyclopropylmethyl)-$\alpha$-(1,1-dimethylethyl)-4,5-epoxy-18, 19-dihydro-3-hydroxy-6-methoxy-$\alpha$-methyl-6,14-ethenomorphinan-7-methanol. Buprenorphine is manufactured and sold as buprenorphine HCl by Reckitt Benckiser Pharmaceuticals (Richmond, Va., sold as Buprenex (injectable; analgesic); Subutex (sublingual tablets; opioid addiction)). Buprenorphine is also manufactured and sold as Suboxone, a combination of buprenorphine HCl and naloxone HCl dehydrate in a ratio of 4:1. Suboxone, like Subutex, is generally used in treating opioid addiction and as an analgesic.

Buprenorphine is usually administered intravenously and sublingually. As an analgesic, buprenorphine may be administered intravenously in relatively low doses, e.g., 0.3-0.6 mg/injection. In treating opioid addiction, buprenorphine (e.g., alone or in combination with naloxone) may be administered sublingually in doses upwards of from about 0.5 mg-32 mg/day, for example, about 0.5, 1.0 2.0, 4.0, 8.0, 24, or 32 mg/day. An effectiveness plateau may be reached at about 32 mg/day. Higher doses for treating opioid addiction may be required as a result of opioid experience and therefore tolerance of addicted individuals. Here administration of buprenorphine by other modes are also contemplated.

In another variation, kappa opioids other than buprenorphine are employed. For example, kappa receptor agonists and antagonists may be used. Suitable kappa receptor agonists include without limitation, butorphanol, BRL-52537, cyclazocine, enadoline, GR-89696, HZ-2, ICI-204,448, ketazocine, LPK-26 (2-(3,4-Dichlorophenyl)-N-methyl-N-[(1S)-1-(2-isopropyl)-2-(1-(3-pyrrolinyl))ethyl]acetamide), nalbuphine, pentazocine, salvinorin A, spiradoline, tifluadom, U-50488, U-62066, U-69593, and combinations thereof. Exemplary kappa receptor antagonists for use in the compositions include without limitation, 5'-guanidinonaltrindole, norbinaltorphimine, JDTic, and combinations thereof.

Other Active Agents

In some variations, buprenorphine is administered in combination with an opioid antagonist. Suitable opioid antagonists that may be used without limitation include natrexone and naloxone. Naltrexone can be administered intravenously in doses of 0.2 mg-0.6 mg; subcutaneously 0.8 mg; and intramuscularly 380 mg/week. Naltrexone can also be administered orally or sublingually in doses of about 0.25 mg to about 8.0 mg, for example, about 1.0 mg, 2.0 mg, 4.0 mg or 8.0 mg. Naloxone is available for intravenous, intramuscular or subcutaneous administration, in concentrations from about 0.4 mg/mL to 1.0 mg/mL. In some variations, the opioid antagonist is provided with the partial opioid agonist, e.g., buprenorphine, in a single dosage form.

In some variations, the kappa receptor antagonist, e.g., buprenorphine, is administered in combination with a mood stabilizer. Mood stabilizers for use here include without limitation, lithium, aripiprazole (Abilify), olanzapine (Zyprexa), risperidone (Risperidal), quietiapine (Seroquel), and ziprasidone (Geodon). Therapeutic doses of lithium may be about 300-1800 mg/day, for example, about 900-1200 mg/day. Specifically, lithium doses of about 300 mg, about 600 mg, or about 900 mg per day may be useful. Therapeutic doses of ziprasidone may be about 20-160 mg/day, for example, about 80-160 mg/day. Specifically, ziprasidone doses of about 40 mg, about 80 mg, or about 120 mg per day may be useful. The therapeutic doses of aripiprazole may be about 1-30 mg/day, for example, about 5-20 mg/day or about 10-15 mg/day. Specifically, aripriprazole doses may be about 2.0 mg, about 10 mg, or about 15 mg per day.

In some variations, the partial opioid agonist, e.g., buprenorphine, may be administered in combination with an antipsychotic agent. The antipsychotic agents may be any class of antipsychotic, e.g., it may be a typical or atypical antipsychotic. Some antipsychotic agents may have sedative effects on the patient, and facilitate sleep. For instance, phenothiazines, thioxanthenes, and other heterocyclic compounds can all be administered in combination with buprenorphine.

Phenothiazines that may be used include without limitation: chloropromazine hydrochloride, mesoridazine hydrochloride, thioridazine hydrochloride (Mellaril), fluphenazine hydrochloride (Prolixin), fluphenazine enanthate, fluphenazine decanoate, perphenazine, trifluoperazine hydrochloride (Stelazine), and combinations thereof. Other unlisted phenothiazine antipsychotics and analogs thereof can also be used.

Phenothiazines possessing relatively high sedative effect include without limitation: chlorpromazine hydrochloride (Largactil, Thorazine), mesoridazine hydrochloride, and thioridazine hydrochloride. In relation to these, perphenazine possesses a somewhat lower sedative effect.

Therapeutic doses for chlorpromazine hydrochloride may be about 30-2000 mg/day, for example, about 200-800 mg/day. Therapeutic doses for mesoridazine hydrochloride are about 30-400 mg/day, for example, about 75-300 mg/day. Therapeutic doses for thioridazine hydrochloride are about 20-800 mg/day, for example, about 15-600 mg/day. Perphenazine is administered in a therapeutic dose range of about 4-64 mg/day, for example, about 8-32 mg/day.

Thioxanthenes for use in the present invention include chloroprothixene, thiothixene hydrochloride (Navane), clopenthixol, cis-flupentixol, and pitflutixol. Other unlisted thioxanthene antipsychotics and analogs thereof can also be used.

Chloroprothixene is administered in a therapeutic dose range of about 30-600 mg/day, for example, about 50-400 mg/day. Chloroprothixene possesses moderately high sedative effects.

Other antipsychotic compounds, including other heterocyclic antipsychotic compounds for use herein may include without limitation: abripiprazole, arisulpride, clozapine, quetiapine fumarate, haloperidol, loxapine succinate (Loxapac, Loxitane), clothiapine, metiapine, zotepine, molindone hydrochloride, olanzapine, paliperidone, pimozide, prochlorperazine (Compazine, Buccastem, Stemetil or Phenotil) risperidone, trifluoroperazine, zuclopenthixol (Clopixol), and combinations thereof. Other unlisted antipsychotics and analogs thereof can also be used.

When olanzapine is used, it may be provided in a dose of about 5.0 mg, about 10 mg, or about 15 mg, or combinations thereof. When paliperidone is provided, it may be provided in a dose of about 1.5 mg, about 3.0 mg, about 6.0 mg, or about 12 mg, or combinations thereof. With respect to quietiapine, it may be provided in a dose of about 50 mg, 100 mg, 300 mg, or combinations thereof. When risperidone is used, it may be provided in a dose of about 0.25 mg, about 0.5 mg, about 1.0 mg, about 2.0 mg, about 3.0 mg, about 4.0 mg, or combinations thereof. When arisulpride is used, it may be provided in a dose of about 50 mg, about 200 mg, or combinations thereof (between about 400-800 mg/day). When trifluoroperazine is used, it may be provided in doses of about 1.0 mg, 2.0 mg, 5.0 mg, 10 mg, or combinations thereof.

In some variations, buprenorphine is administered in combination with ziprasidone (Geodon). Ziprasidone can be administered in a therapeutic dose range of about 20-160 mg/day, for example, about 80-160 mg/day. Ziprasidone may be a favorable antipsychotic because it is hepatically metabolized by aldehyde oxidase. Only minor metabolism occurs via CYP3A4 so there is a decreased likelihood of interactions from medications that induce or inhibit this enzyme (e.g., buprenorphine). Also, compared to other atypical antipsychotics, namely olanzapine, ziprasidone has a benign metabolic side effect profile with less likelihood of medication-induced weight gain, dyslipidemia, and insulin resistance leading to diabetes. Because the prevalence of the metabolic syndrome and obesity in patients with bipolar disorder is even higher than the already very high prevalence that has been estimated for the U.S. general population, the use of drugs which are metabolically neutral may therefore be beneficial.

In some variations, buprenorphine is administered in combination with aripiprazole (Abilify). Aripiprazole can be administered in a therapeutic dose range of about 1-30 mg/day, for example, about 5-20 mg/day or about 10-15 mg/day. Aripiprazole is another favorable antipsychotic because, similar to ziprasidone, it has a benign metabolic side effect profile.

In some variations, buprenorphine is administered in combination with quetiapine fumurate (Seroquel). Quetiapine fumurate can be administered in a therapeutic dose range of about 50-750 mg/day, for example, about 300-500 mg/day.

Clozapine can be administered in a therapeutic dose range of about 12.5-900 mg/day, for example, about 150-450 mg/day. Aripiprazole can be administered in a therapeutic dose range of 1-30 mg/day, for example, about 5-20 mg/day or about 10-15 mg/day. Clozapine and quetiapine fumurate exert moderately high sedative effects. Aripriprazole and ziprasidone possess relatively low sedative effects.

In other variations, the partial opioid agonist, e.g., buprenorphine, is administered in combination with an antiepileptic or an anticonvulsant. Exemplified antiepileptic agents include topiramate, zonisamide and the like. Anticonvulsant agents may have sedative effects on the patient, and facilitate sleep. Anticonvulsants or antiepileptics for use herein along with their therapeutic doses include without limitation the following classes of compounds: barbiturates (e.g., phenobarbitol (150-300 mg/day) and mephobarbitol), hydantoins (e.g., phenyloin (300-1000 mg/day)), iminostilbenes (e.g., carbamazepine (400-1600 mg/day) and oxcarbazepine (450-2400 mg/day)), and succinimides (e.g., ethosuximide (250-2000 mg/day)). Other useful anti-convulsants/epileptic compounds include: gabapentin (300-3600 mg/day), topiramate (50-1600 mg/day), tiagabine (4-56 mg/day), levetiracetam (1000-3600 mg/day), felbamate (1200-3600 mg/day), zonisamide (100-600 mg/day), and valproic acid (10-100 mg/kg/day). Divalproex, lamotrigine, and oxcarbazine may also be used. Divalproex may be provided in doses of about 1000 mg, about 1500 mg, or about 2000 mg, or combinations thereof. Lamotrigine may be provided in doses or about 50 mg, about 100 mg, about 200 mg, or combinations thereof.

Drowsiness is a side effect of the barbiturates, as a class, and gabapentin, topiramate, ethosuximide, zonisamide, tiagabine. A side effect of carbamazepine, after long term treatment, may be drowsiness.

In some variations, the partial opioid agonist, e.g., buprenorphine, is administered in combination with muscle relaxant. Muscle relaxants for use in the present invention include: carisoprodol (1000-1400 mg/day), meprobamate (200-2400 mg/day), baclofen (15-80 mg/day), and tizanidine (4-36 mg/day).

In some variations, the partial opioid agonist, e.g., buprenorphine, is administered in combination with ziprasidone (Geodon) and carisoprodol.

In some variations, the partial opioid agonist is administered in combination with an agent that potentiates its pharmacological effect, for example, an agent that competes with the P-450 enzymes that metabolizes the partial opioid agonist.

P-450 CYP3A4 or CYP2D6 Inhibitors (Buprenorphine Potentiators)

Buprenorphine is primarily metabolized by the cytochrome P450 enzymes CYP3A4 and CYP2D6. Therefore, administering buprenorphine in combination with an inhibitor of CYP3A4 and or CYP2D6 may potentiate the pharmacological effect of buprenorphine (e.g., by enhancing bioavailability). Combined administration of an inhibitor of CYP3A4 and/or CYP2D6 with buprenorphine (either as separate dosage forms or in a single dosage form) may allow for administration of fewer therapeutically effective doses of buprenorphine and/or for administration of subtherapeutic doses of buprenorphine.

In some variations, buprenorphine is administered in combination with or co-formulated with a CYP3A4 inhibitor as a second active agent. Exemplary CYP3A4 inhibitors include, without limitation, amiodarone, cannabinoids (e.g., dronabinol, nabilone, and Sativex), cimetidine, clarithromycin, delavirdine, erythromycin, fluconazole, indinavir, itraconazole, ketoconazole, metronidazole, miconazole, nefazadone, nelfinavir, nicardipine, norfloxacin, omeprozol, quinine, ritonavir, saquinavir, verapamil, zafirlukast and zileuton.

In some variations, buprenorphine is administered with a 2D6 inhibitor, e.g., cimetidine (Zantac). In some variations, the cimetidine is administered at doses above 200 mg, for example, about 300 mg, 400 mg, 600 mg or 800 mg. In other variations, buprenorphine is administered with a CB1 and CB2 agonist (e.g., Cannabinor and KN38-7271) or a CB1 antagonist (e.g., Taranabant, Otenabant, Ibibipinabant, Surinabant, and Drinabant).

In other variations, buprenorphine is administered in combination with or co-formulated with a CYP2D6 inhibitor as a second active agent. Exemplary CYP2D6 inhibitors include, without limitation, quinidine, terbinafine, celecoxib, chlorpheniramine, chlorpromazine, clemastine, clomipramine, cocaine, amiodarone, diphenhydramine, doxorubicin, goldenseal, halofantrine, histamine H1 receptor antagonists, hydroxyzine, levomepromazine, metoclopramide, mibefradil, midodrine, moclobemide, perphenazine, ranitidine, red-haloperidol, ritonavir, ticlopidine, and tripelennamine.

The CYP3A4 and/or CYP2D6 inhibitors are administered at their recommended or smaller doses for their approved uses. See, e.g., Goodman and Gilman's, supra, Physician's Desk Reference, supra, and the FDA Orange Book.

Sugar

It has been reported that glucose and sucrose ingestion induces production of endogenous opioids, which may alleviate opioid withdrawal symptoms. See, e.g., Kracke, et al., *Anesth Analg* (2005) 101:64-8; Gharavi, et al., *Pediatr Int*

(2007) 49:652; Jain, et al., *Brain Res Bull.* (2004) 64:319-22; and Calantuoni, et al., *Obesity Res* (2002) 10:478. Glucose administration can also alleviate opioid-induced memory loss. See, e.g., Ragozzino, et al., *Brain Res* (1994) 655:77-82; Ragozzino, et al., *J Neurosci* (1998) 18:1595-1601; and Talley, et al., *Neurobiol Learn Mem* (1999) 71:62-79. Sugars are also useful for the transdermal delivery of opioids. See, e.g., U.S. Pat. No. 4,956,171 and PCT Publ. No. WO98/54196.

Accordingly, in some variations, the partial opioid agonist, e.g., buprenorphine, is administered in combination with glucose or sucrose. The sugar can be in a solid or liquid form, as desired. For example, the partial opioid agonist, e.g., buprenorphine, is co-administered with a concentrated glucose or sucrose solution, or formulated with glucose or sucrose in sufficient amounts to induce induction of endogenous opioids and/or to delay or alleviate withdrawal symptoms. In some variations, glucose is co-administered at a concentration of about 100 mg/kg. In some variations, sucrose is co-administered in a solution containing at least about 20% sucrose, for example, about 25%, 30%, 35% sucrose solution.

Supplements/Additional Agents

In some variations, the partial opioid agonist, e.g., buprenorphine, is administered in combination with one or more supplements. The supplements may, for example, be used to treat a comorbid condition, counteract any undesirable side effects of the partial opioid agonist or any other co-administered pharmacological agent, or counter nutritional deficiencies in the subject being treated.

In some variations, the supplement counteracts the side effect of constipation. For example, the partial opioid agonist can be co-administered or formulated with fiber or a bulking agent (e.g., psyllium, inulin), a stool softener or a laxative.

In other variations, the supplement is used to counteract extrapyrimidal side-effects. Here the supplement may include an antihistamine, an anticholinergic, or combinations thereof. Exemplary antihistamines include without limitation, certrizine, diphenydramine, fenofexadine, loratidine, and combinations thereof.

In some variations, the supplement counteracts a nutritional deficiency. For example, the partial opioid agonist can be co-administered or formulated with one or more B vitamins, e.g., thiamin (B-1), riboflavin (B-2), niacin, pyridoxine (B-6), folic acid, cobalamin (B-12), biotin, and/or pantothenic acid. In some variations, one or more of vitamins A, C, D, E or K is co-administered with the partial opioid agonist. In some variations, the partial opioid agonist is co-administered or co-formulated with one or more of calcium, iron, zinc, selenium, magnesium, manganese, copper and/or chromium. In some variations, the partial opioid agonist is co-administered or co-formulated with an antioxidant, e.g., lycopene, acetylcysteine.

In other variations, the supplement or additional agent is used to treat a comorbid condition. For example, the comorbid condition may be diabetes, obesity, or fibromyalgia. When diabetes is the comorbid condition, the additional agent may be metformin. When the comorbid condition is obesity, the additional agent may be metformin, topiramate, or combinations thereof. When the comorbid condition is fibromyalgia, the additional agent may be carisoprodol, colchicine, cyclobenzaprine, duloxetine, gabapentin, guafenisin, interferon, methocarbamol, pregabalin, probenecid, sulfinpyrazone, vitamin B12, or combinations thereof.

In some variations, the partial opioid agonist is administered in combination with or co-formulated with an opioid abuse deterrent agent, for example, an opioid antagonist.

Abuse deterrent agents find use that are healthful or benign when co-administered at low concentrations, but produce undesirable or unpleasant side effects when co-administered at higher concentrations, for example, when a patient attempts to administer more than the prescribed dose of the partial opioid agonist. For example, niacin at low doses (e.g., 10-50 mg) serves as a B vitamin supplement, but at higher doses will cause flushing. Acetylcysteine at low doses serves as an antioxidant, but at higher doses, the sulfur content has a noticeable and unpleasant smell. Glucose or sucrose administered at lower doses will potentiate the effects of the partial opioid agonist, as discussed above, but at higher doses will cause unpleasant side effects, for example, due to high levels of insulin release.

Other sulfur-containing compounds find use as abuse deterrent agents. Nociceptive agents also find use as abuse deterrent agents, for example, capsaicin, chili pepper and other hot pepper extracts.

It may be important here to mention that in the methods, compositions, and kits described here, some agents may not contemplated for combination with the opioid agonists. In some variations, the partial opioid agonist, e.g., buprenorphine, may be administered to a subject without administering in combination an antidepressant. It is unfavorable to administer antidepressants to patients who are subject to manic or hypomanic episodes, including individuals with bipolar disorder, because all antidepressants can precipitate or exacerbate mania or hypomania.

Antidepressant compounds excluded include, for example, atypical antidepressants (e.g., atomoxetine, bupropion, duloxetine, mirtazapine, nefazodone and trazodone), tricyclic antidepressants (e.g., amineptine, amitriptyline, clomipramine, desipramine, doxepin, dothiepin, imipramine, nortriptyline, protriptyline, trimipramine, lofepramine, amoxapine and the muscle relaxant cyclobenzaprine), monoamine oxidase inhibitors (e.g., phenelzine, tranylcypromine, and selegiline), norepinephrine reuptake inhibitors (e.g, amitriptyline, clomipramine, doxepin, imipramine, trimipramine, amoxapine, desipramine, maprotiline, nortriptyline and protriptyline), serotonin-norepinephrine reuptake inhibitors (e.g., milnacipran, mirtazapine, duloxetine, venlafaxine and sibutramine), norepinephrine-dopamine reuptake inhibitors (e.g., amineptine, modafinil and bupropion), and selective serotonin reuptake inhibitors (e.g., citalopram, escitalopram, fluoxetine, fluvoxamine, paroxetine, and sertraline).

In other variations, the partial opioid agonist may be administered to a subject without administering in combination a benzodiazepine. Benzodiazepines excluded include, for example, alprazolam (Xanax), valium, diazepam, temazepam (Restoril), lorazepam, chlordiazepoxide (Librium) and clonazepam (Klonopin).

Dosage Forms

Also described here are pharmaceutical compositions comprising a partial opioid agonist, a second active agent, and/or an additional/supplemental agent. The compositions may include a mixture of an effective amount of a partial opioid agonist (e.g., buprenorphine) and one or more opioid antagonist(s) and/or one or more antipsychotic(s) and/or one or more anticonvulsant(s) and/or one or more antiepileptic(s) and/or one or more muscle relaxant(s) agents and/or one or more mood stabilizer(s). The partial opioid agonist and/or the combined pharmacological agents, i.e., opioid antagonist(s), antipsychotic(s), anticonvulsant(s), antiepileptic(s), muscle relaxant(s), may be included in therapeutic or subtherapeutic doses. In some variations, the compositions comprise one or both pharmacological agents in subtherapeutic doses. The compositions can be co-formulated with one or more opioid potentiators, supplements and/or opioid deterrent agents, as discussed above.

In some variations, the pharmaceutical compositions comprise one or more opioid antagonists. In one variation, the pharmaceutical composition comprises naltrexone. In another variation, the pharmaceutical composition comprises naloxone.

In some variations, the pharmaceutical compositions comprise one or more antipsychotics. The antipsychotic may include without limitation, a phenothiazine, a thioxanthene, or other heterocyclic compounds and prodrugs thereof. In one variation, the pharmaceutical composition comprises one or more antipsychotics selected from the group of quetiapine, aripiprazole, clozapine and ziprasidone. Additional antipsychotics can find use, for example, those described herein. In one variation, the pharmaceutical composition comprises subtherapeutic amounts of antipsychotic(s).

In some variations, the pharmaceutical compositions comprise one or more anticonvulsants(s)/antiepileptic(s). The anticonvulsant/antiepileptic can be selected from barbiturates, hydantoins, iminostilbenes, succinimides, valproic acid and prodrugs thereof. Additional anticonvulsants can find use, for example, those described herein. In one variation, the pharmaceutical composition comprises one or more anticonvulsive(s)/antiepileptic(s) in subtherapeutic amounts.

In some variations, the pharmaceutical compositions comprise one or more mood stabilizer(s) and the prodrugs thereof. In one variation, the pharmaceutical composition comprises one or more mood stabilizer selected from the group of lithium and ziprasidone. Additional mood stabilizer can find use, for example, those described herein. In one variation, the pharmaceutical composition comprises one or more mood stabilizers in a subtherapeutic amount.

In some variations, the pharmaceutical compositions comprise one or more muscle relaxant(s) and the prodrugs thereof. In one variation, the pharmaceutical composition comprises the muscle relaxant carisoprodol. Additional muscle relaxants can find use, for example, those described herein. In one variation, the pharmaceutical composition comprises one or more muscle relaxant(s) in a subtherapeutic amount.

A combination of partial opioid agonist (e.g., buprenorphine) and/or one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) agents can be administered to a subject, e.g., a human patient, a domestic animal such as a dog or a cat, independently or together in the form of a pharmaceutically acceptable salts, or in the form of a pharmaceutical composition where the compounds are mixed with suitable carriers or excipient(s) in an effective amount.

A combination of partial opioid agonist (e.g., buprenorphine) and/or one or more opioid antagonists and/or one or more antipsychotic(s) and/or one or more anticonvulsant(s) and/or one or more antiepileptic(s) and/or one or more muscle relaxant(s) and/or one or more mood stabilizer(s) agents of this invention can be incorporated into a variety of formulations for therapeutic administration. More particularly, a combination of the present invention can be formulated into pharmaceutical compositions, together or separately, by formulation with appropriate pharmaceutically acceptable carriers or diluents, and can be formulated into preparations in solid, semi-solid, liquid or gaseous forms such as tablets, capsules, pills, powders, granules, dragees, gels, slurries, ointments, solutions, suppositories, patches, films, injections, inhalants, and aerosols.

Suitable formulations for use in the present invention are found in, for example, in *Remington: The Science and Practice of Pharmacy,* 21$^{st}$ Ed., 2005; *Martindale: The Complete Drug Reference,* Sweetman, 2005, London: Pharmaceutical Press; Niazi, *Handbook of Pharmaceutical Manufacturing Formulations,* 2004, CRC Press; and Gibson, *Pharmaceutical Preformulation and Formulation: A Practical Guide from Candidate Drug Selection to Commercial Dosage Form,* 2001, Interpharm Press, which are hereby incorporated by reference herein. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

The pharmaceutical preparations of the present invention can be prepared for delivery in a sustained-release, controlled release, extended-release, timed-release or delayed-release formulation, for example, in semi-permeable matrices of solid hydrophobic polymers containing the effective agent(s). Various types of sustained-release materials have been established and are well known by those of skill in the art. Current extended-release formulations include film-coated tablets, multiparticulate or pellet systems, matrix technologies using hydrophilic or lipophilic materials and wax-based tablets with pore-forming excipients (see, for example, Huang, et. al., *Drug Dev. Ind. Pharm.* 29:79 (2003); Pearnchob, et. al., *Drug Dev. Ind. Pharm.* 29:925 (2003); Maggi, et. al., *Eur. J. Pharm. Biopharm.* 55:99 (2003); Khanvilker, et. al., *Drug Dev. Ind. Pharm.* 228:601 (2002); and Schmidt, et. al., *Int. J. Pharm.* 216:9 (2001). Sustained-release delivery systems can, depending on their design, release the compounds over the course of hours or days, for instance, over 4, 6, 8, 10, 12, 16, 20, 24 hours or more. Sustained release formulations can be prepared using naturally-occurring or synthetic polymers, for instance, polymeric vinyl pyrrolidones, such as polyvinyl pyrrolidine (PVP); carboxyvinyl hydrophilic polymers; hydrophobic and/or hydrophilic hydrocolloids, such as methylcellulaose, ethylcellulose, hydroxypropylcellulose, and hydroxypropylmethylcellulose; and carboxypolmethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a combination of partial opioid agonist (e.g., buprenorphine) and/or one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) agents of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a combination of partial opioid agonist (e.g., buprenorphine) and/or one or more opioid antagonist(s) and/or one or more antipsychotic(s) and/or one or more antipsychotic(s) and/or one or more anticonvulsant (s) and/or one or more antiepileptic(s) and/or one or more muscle relaxant(s) and/or one or more mood stabilizer(s) agents can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, a combination of partial opioid agonist (e.g., buprenorphine) and one or more mood stabilizers, one or more antipsychotics and/or one or more anticonvulsants and/or one or more antiepileptics and/or one or more muscle relaxant(s) agents can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a combination of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one variation, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in a conventional manner.

In addition to the formulations described previously, a combination of partial opioid agonist (e.g., buprenorphine) and/or opioid antagonist(s) and/or one or more antipsychotics and/or one or more anticonvulsants and/or one or more antiepileptics and/or one or more muscle relaxant(s) and/or one or more mood stabilizer(s) agents of the present invention can also be formulated as a depot preparation. Such long acting formulations can be administered by implantation (for example subcutaneously or intramuscularly), or by needle-free injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

II. Kits

The compositions described here may be provided in a kit. Kits for treating mania associated with opioid withdrawal may include a plurality of buprenorphine dosage forms and instructions for administering the dosage forms according to a predetermined dosage regimen. Here the predetermined dosing regimen may include administering a first buprenorphine dose and at least one additional buprenorphine dose that is less than the first dose. The predetermined dosing regimen may provide that the first dose be administered in the morning, e.g., at 6 am or between about 6 am and 9 am, and the at least one additional dose administered in the afternoon, e.g., at 12 pm (noon) or between about 12 pm and 3 pm, evening, e.g., at 6 pm or between about 6 pm and 9 pm, or late evening, e.g., at 12 am (midnight).

The aforementioned kits may include a housing configured to organize the dosage forms according to the predetermined dosing regimen. For example, the housing may be configured to organize the plurality of dosage forms into morning dosage forms and evening dosage forms. In some variations, the housing may be configured to organize the plurality of buprenorphine dosage forms according to a rapidly or a gradually decreasing dosing regimen. In yet further variations, the housing may be configured to organize the buprenorphine dosage forms according to the day of the week to be taken.

The kits may also include a second dosage form having one or more second active agents. The second active agent may also help to stabilize the mood of the patient. Exemplary second active agents include without limitation, aripriprazole, arisulpride, olanzapine, paliperidone, quetiapine, risperidone, ziprasidone, and combinations thereof. The kit may further include additional dosage forms that include one or more additional agents for treating a comorbid condition. For example, an antihistamine may be useful to include when the comorbid condition is a sleep disorder. Dosage forms that include other active agents (e.g., to treat comorbidities) or second active agents (e.g., for mood stabilization) may be organized in the housing similar to the organization provided for the buprenorphine dosage forms, as described above.

Kits for treating the symptom of racing thoughts in bipolar disorder may include a plurality of buprenorphine dosage forms, at least one second dosage form comprising a second active agent that helps to stabilize mood, e.g., an atypical antipsychotic agent, and instructions for taking the dosage forms according to a predetermined dosing regimen. Dosage forms including an opioid antagonist such as naloxone may also be included. In some variations, dosage forms having a supplemental or additional agent for treating a comorbid condition, side-effect of second agent, and/or other symptoms of bipolar disorder may be provided in the kits.

These kits may also further include a housing configured to organize the dosage forms according to the predetermined dosing regimen. For example, the housing may be configured to organize the plurality of dosage forms into morning dosage forms and evening dosage forms. In some variations, the housing may be configured to organize the plurality of dosage forms according to a rapidly or a gradually decreasing dosing regimen. In yet further variations, the housing may be configured to organize the dosage forms according to the day of the week to be taken. The kits may also be tailored to treat particular bipolar conditions or subtypes. For example, the kits may be tailored to treat bipolar I disorder, bipolar II disorder, mixed bipolar disorders, rapidly-cycling bipolar disorder, acute mania, drug-induced mania, hypomania, cyclothymia, or combinations thereof.

In some variations, the kits comprise a partial opioid agonist (e.g., buprenorphine) and/or one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) agents in separate formulations or dosage forms. In other variations, the kits comprise a partial opioid agonist (e.g., buprenorphine) and/or one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) agents within the same formulation or dosage form.

In further variations, the kits may provide the of partial opioid agonist (e.g., buprenorphine) and/or one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) agents independently in uniform dosage formulations throughout the course of treatment. In some variations, the kits provide the of partial opioid agonist (e.g., buprenorphine) and/or one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) agents independently in graduated dosages over the course of treatment, either increasing or decreasing, according to the requirements of the subject or according to a predetermined dosing regimen.

In some variations, the kits comprise a partial opioid agonist, buprenorphine. In one variation, the kit comprises compositions comprising a subtherapeutic amount of buprenorphine.

In some variations, the kits comprise compositions comprising one or more opioid antagonist(s). In one variation, the opioid antagonist is naloxone.

In other variations, the kits comprise dosage forms comprising one or more antipsychotic(s). The antipsychotics can be selected from a phenothiazine, a thioxanthene, or other heterocyclic compounds. In one variation, the kit comprises one or more antipsychotics selected from the group of quetiapine, aripiprazole, clozapine and ziprasidone. In one variation, the kit comprises compositions comprising antipsychotic(s) in a subtherapeutic amount.

In one variation, the kit comprises one or more mood stabilizers. In one variation, the kit comprises a mood stabilizer selected from the group consisting of lithium and ziprasidone. In one variation, the kit comprises compositions comprising mood stabilizer(s) in a subtherapeutic amount.

In one variation, the kits comprise of anticonvulsant/antiepileptic agents. In some variations, the kit comprises one or more anticonvulsants/antiepileptics that are barbiturates, hydantoins, imminostilbenes and/or succinimides. In one variation, the kit comprises subtherapeutically effective amounts of anticonvulsant/antiepileptic agent(s).

In some variations, the kits comprise muscle relaxant(s). In some variations, the kit comprises the muscle relaxant carisoprodol. In one variation, the kit comprises compositions comprising muscle relaxant(s) in a subtherapeutic amount.

The kits may also comprising a housing configured to organize the dosage forms according to a predetermined dosing regimen. For example, the housing may be configured to organize the plurality of dosage forms into morning dosage forms and evening dosage forms. The housing may also be configured to organize the plurality of buprenorphine dosage forms according to a rapidly or a gradually decreasing dosing regimen.

III. Methods

The methods described here may find use in the treatment and prevention of mood disorders involving manic episodes. In particular, the methods may find use in the amelioration, inhibition, reduction and prevention of symptoms indicative of a manic episode or hypomanic episode, e.g., racing thoughts, as described herein. Exemplified general categories of disorders treatable by the present methods and compositions include, without limitation, bipolar disorder, mania and manic episodes, hypomania, cyclothymia, and drug-induced mania, among others. The methods promote and facilitate regular sleep patterns in individuals subject to manic or hypomanic episodes. The methods may also treat or prevent manic or hypomanic episodes occurring in these disorders in subjects afflicted with concurrent substance addiction and/or withdrawal from substances of abuse.

For example, during opioid withdrawal, many adverse withdrawal symptoms may occur. Physical manifestations often include sweating, nausea, chills, diarrhea, papillary dilation, piloerection, tachycardia, increased blood pressure, hypersensitivity to pain, stomach cramps, and muscle cramps. Psychological manifestations of opioid withdrawal include dysphoria, restlessness, irritability, mania, anxiety, and depression. Due to the often severe nature of the withdrawal symptoms, individuals who are addicted to or dependent on opioids often choose to remain addicted or dependent rather than seek treatment. This may present significant inhibition to an individual being able to overcome his/her addiction. The methods here address this need by providing methods for preventing or inhibiting these withdrawal symptoms, especially mania triggered experienced during opioid withdrawal. Therapeutic or subtherapeutic amounts of buprenorphine may be administered to treat or prevent opioid withdrawal induced mania.

As previously stated, the treatment regimens may achieve mood stabilization by administering a partial opioid agonist, e.g., buprenorphine, in a predetermined fashion. The amounts and frequency of administration of the partial opioid agonist will vary depending on such factors as the particular type of bipolar disorder diagnosed, associated symptoms and/or comorbidities, other medications being taken by the patient, and previous history of opioid abuse. For example, when a plurality of buprenorphine doses are administered per day, the first dose may be higher than any additional dose given. In some variations, a morning dose of buprenorphine may be higher than a buprenorphine dose given in the evening or late evening. For example, a buprenorphine dose administered at 6 am may be higher than a buprenorphine dose given in the evening, e.g., at 6 pm, or late evening, e.g., at 12 am (midnight). In some variations, the treatment regimens may include rapidly decreasing the buprenorphine dose over the course of a day. In other variations, a gradual decrease in the buprenorphine dose is employed (over a day). Exemplary (predetermined) dosing regimens are shown below in Table 1.

TABLE 1

Exemplary Dosing of Buprenorphine For Treatment of Mania Associated With Opioid Withdrawal

| First Dose (e.g., morning dose at 6 am) in mg | Additional Dose (e.g., 12 pm) in mg | Additional Dose (e.g., evening dose at 6 pm) in mg | Additional Dose (e.g., late evening dose at 12 am) in mg |
|---|---|---|---|
| 32 | 0 | 0 | 0 |
| 24 | 0 | 0 | 0 |
| 24 | 4 | 2 | 1 |
| 16 | 0 | 0 | 0 |
| 16 | 8 | 0 | 0 |
| 16 | 8 | 4 | 0 |
| 16 | 8 | 4 | 2 |
| 16 | 4 | 2 | 1 |
| 8 | 8 | 0 | 0 |
| 8 | 4 | 4 | 0 |
| 8 | 4 | 2 | 1 |
| 4 | 0 | 0 | 0 |
| 4 | 4 | 4 | 0 |
| 4 | 2 | 1 | 0 |
| 4 | 2 | 1 | 0.5 |
| 2 | 0 | 0 | 0 |
| 2 | 2 | 2 | 0 |
| 2 | 2 | 1 | 0 |
| 2 | 2 | 1 | 0.5 |

In some variations, the treatment regimens may include rapidly decreasing the buprenorphine dose over the course of a day. In other variations, a gradual decrease in the buprenorphine dose is employed (over a day). The treatment regimens may be useful in treating mama associated with opioid withdrawal. As previously stated, the inventors believe that when higher doses of buprenorphine are taken in the evening, it acts as a mood destabilizer and thus, kindles mania or mania-like symptoms in this patient population. In another variation, the treatment regimens may be beneficial in alleviating racing thoughts during the depressive phase of bipolar disorder.

In Table 1, certain doses of buprenorphine are shown as 0 mg. In these instances, a dosage form may be administered that includes a carrier, filler, second active agent, supplemental/additional agent, etc., but it will lack buprenorphine. In other instances, no dosage form may be administered.

When a second active agent is administered with buprenorphine (or another partial opioid agonist), it may also be administered in a rapidly or gradually increasing or decreasing manner throughout the day. In some variations, the second active agent is administered in an increasing manner, i.e., the morning dose is lower than the evening or late evening dose. In other variations, the dosing of the second active agent and partial opioid agonist is inverse to one another.

Administered dosages for partial opioid agonists, e.g., buprenorphine, opioid antagonist(s), antipsychotic(s), mood stabilizer(s), anticonvulsant(s), antiepileptic(s), and muscle relaxant(s) are in accordance with dosages and scheduling regimens practiced by those of skill in the art. For example, buprenorphine may be administered daily in doses of about 2 mg, about 4 mg, about 6 mg, about 8 mg, about 10 mg, about 12 mg, about 14 mg, about 16 mg, about 18 mg, about 20 mg, about 22 mg, about 24 mg, about 26 mg, about 28 mg, about 30 mg, or about 32 mg. In some variations, when a higher dose of buprenorphine is administered, a high dose of mood stabilizer is also administered. General guidance for appropriate dosages of all pharmacological agents used in the present methods is provided in Goodman and Gilman's *The Pharmacological Basis of Therapeutics*, $11^{th}$ Edition, 2006, supra, in a Physicians' Desk Reference (PDR), for example, in the $62^{nd}$ (2008) Ed., Thomson PDR, and in the FDA Orange Book, which are hereby entirely incorporated by reference herein. In the compositions and methods of the present invention, efficacious dosages of opioid partial agonist(s), opioid antagonist(s), antipsychotic(s), mood stabilizer(s), anticonvulsant(s), antiepileptic(s), and muscle relaxant(s) for practicing the present invention can be equal to or less than (e.g., about 25, 50, 75, or 100%) the dosages published for other indications. Combining an opioid partial agonist with a mood stabilizer, an antipsychotic, a mood stabilizer, an anticonvulsant, an antiepileptic or a muscle relaxant allows for both pharmacological agents to be administered at subtherapeutic doses and elicit an efficacious effect in reducing or preventing the symptoms of a manic episode.

The appropriate dosage of partial opioid agonists (buprenorphine), opioid antagonist(s), antipsychotic(s), mood stabilizer(s), anticonvulsant(s), antiepileptic(s), and muscle relaxant agent(s) will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient. Patients who have not before been exposed to opioids will require lower doses. Patients who have been exposed to opioids, or who have opioid dependence or addiction, will require higher doses.

For the methods of the present invention, subtherapeutic dosages of buprenorphine are administered at doses that are about 25% or less of a full dose for the indicated purposes of buprenorphine. For example, in the present methods buprenorphine is administered in amounts that are about 25%, 20%, 15%, 10%, 5%, 2%, 1% or less than a full dose. Dosing of buprenorphine is known in the art and published in standard reference texts commonly consulted by trained clinicians, including for example, Goodman and Gilman's *The Pharmacological Basis of Therapeutics,* 11th Edition, 2006, supra, in a Physicians' Desk Reference (PDR), for example, in the 62nd (2008) Ed., Thomson PDR, and in the FDA Orange Book. In treating opioid addiction, buprenorphine (e.g., alone or in combination with naloxone) typically is administered sublingually in full doses of from about 2-32 mg/day, for example, about 2, 4, 8, 16 or 32 mg/day. In some embodiments, the subtherapeutic amounts of buprenorphine are administered sublingually, for example, in amounts that are about 25% of a full dose or less, for example, about 20%, 15%, 10%, 5%, 2% of a full dose. In some embodiments, the subtherapeutic amounts of buprenorphine are administered sublingually in doses of from about 0.4-8 mg/day, for example, about 0.4, 1, 2, 4 or 8 mg/day. In some embodiments, standard or full doses of sublingually formulated buprenorphine are administered orally (based on a 20% or ⅕ bioavailability of the sublingual formulation when orally administered).

Generally, in practicing the present methods, effective amounts of one or more partial opioid agonists are administered alone or in combination with and/or one or more opioid antagonist(s), and/or one or more antipsychotic(s) and/or one or more anticonvulsant(s) and/or one or more antiepileptic(s) and/or one or more muscle relaxant(s) and/or one or more mood stabilizers. Co-administered pharmacological agents can be administered together or separately, simultaneously or at different times. When administered, the partial opioid agonist(s), alone or in combination with opioid antagonist(s), antipsychotic(s), mood stabilizer(s), muscle relaxant(s), and/or anticonvulsant(s)/antiepileptic(s) agents independently can be administered once, twice, three, four times daily or more or less often, as needed. In some variations, the administered pharmacological agents are administered once daily. In some variations, the partial opioid agonist is administered at a high dose, alone or in combination with another aforementioned pharmacological agent, in the morning, and then at a lower dose in the evening, for example, before bedtime. This regimen may be less likely to kindle mania and promote drowsiness and sleep. When a mood stabilizer is also employed in the dosing regimen, it may be monodosed, e.g., given before bedtime, or at a multiple times throughout the day.

For certain patients, the methods are carried out concurrently administering the one or more partial opioid agonist and/or then one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s) from the initiation of treatment. For certain patients, the methods are carried out by first administering the one or more partial opioid agonist(s), and then subsequently co-administering the and/or one or more opioid antagonist and/or one or more antipsychotics and/or one or more anticonvulsants and/or one or more antiepileptics and/or one or more muscle relaxant(s) and/or one or more mood stabilizer.

Administration of the partial opioid agonist, for example, buprenorphine, alone or in combination with and/or one or more opioid antagonist and/or one or more antipsychotic(s) and/or one or more anticonvulsant(s) and/or one or more antiepileptic(s) and/or one or more muscle relaxant(s) and/or one or more mood stabilizer(s), can be achieved in various ways, including oral, buccal, parenteral, intravenous, intradermal, subcutaneous, intramuscular, transdermal, transmucosal, intranasal, etc., administration. Buprenorphine, or other partial opioid agonist, can be administered by the same or different route of administration when co-administered with one or more opioid antagonist(s) and/or one or more antipsychotic(s) and/or one or more anticonvulsant(s) and/or one or more antiepileptic(s) and/or one or more muscle relaxant(s) and/or one or more mood stabilizer(s).

In some variations, a partial opioid agonist, for example, buprenorphine, alone or in combination, can be administered in a local rather than systemic manner, for example, transdermally or via another route in a depot or sustained release formulation. In some variations, the partial opioid agonist is administered orally. In some variations, the partial opioid agonist is administered sublingually.

EXAMPLES

The following examples are offered to illustrate the treatment regimens, compositions, and kits described herein.

Example 1

A 35 year old man presented with an addiction to Methadone. Patient was tearful, admitting to feeling depressed and was prone to paroxysms of grandiose and irritable behavior. He had been diagnosed with bipolar disease type I several months ago and was started on Seroquel. Even though he liked the effects of Seroquel on sleep promotion, he only remembered to take it intermittently and instead predominantly used opioid drugs to self-treat prepsychotic and psychotic symptoms. With 8 mg of Suboxone tid, his psychiatric symptoms largely resolved and he began taking the Seroquel regularly, resulting in maximum stabilization of mood fluctuation 1 month later.

Example 2

A 35 year old female with a history of bipolar disease and oxycontin use presented with hypomania as characterized by an expansive, elevated mood, and rapid speech. She had been started on Lithium 300 mg tid but stopped it because she missed her "highs." She was, however, complaining of severe "back pain" for which she wanted a narcotic. She was started on 8 mg of Suboxone bid along with Geodon 40 mg bid and the patient has remained compliant on her medications for over 3 months. On her follow-up visits she demonstrates no manic or hypomanic symptoms.

Example 3

A 45 year old opioid addicted female with schizoaffective disorder and completely noncompliant with her oral psychiatric meds presented in florid psychosis. 2 mg of Suboxone was administered sublingually and the psychosis immediately resolved. Geodon and Lithium were restarted and in combination with psychotherapy, the patient has remained on her medications (including Suboxone) and otherwise drug-free for over 6 months.

Example 4

A 39 year old bipolar female presented with a history of regular crack cocaine use and high doses of intermittent opioids. Previous attempts at initiating an atypical antipsychotic had failed. After starting on Seroquel and Suboxone, she has achieved full remission of symptoms and full return to functioning.

Example 5

A 23 year old male presented with bipolar disorder and prescription drug addiction. He had been unable to tolerate any mood stabilizers or psychotropics. Shortly after starting on Suboxone, Lamictal was begun and the patient remained on therapy with considerable normalization of his mood.

Example 6

A 27 year old male presented with an opioid addiction and bipolar disorder. Although he formerly did not adhere regularly to his medication regimen which included Seroquel and thorazine, once he started Suboxone he became very compliant and his psychiatric symptoms have abated considerably.

Example 7

A 47 year old female with a history of opioid addiction and bipolar disease presented with a mania and was started on lithium 300 mg tid, but stopped it due to intolerable side effects. She was started on Suboxone 8 mg bid and, although she states she does not notice a change from the Suboxone, her mood has normalized. Three months later she continues to do well.

Example 8

A woman presented with a manic episode immediately after her husband's death due to a subdural hematoma after a car accident. The outburst of manic episode that emerges after the death of a close family member is termed bereavement mania in the literature. There was a history of bipolar disorder in the patient which had been previously very well-controlled by 1200 mg of Lithium tid. The DSM IV criteria for manic episode were met even though blood tests showed her lithium levels to be in therapeutic range. She was asking for narcotics to take away her nearly constant headache. She was started on Suboxone 8 mg tid and her mania subsided. A month later the Suboxone was stopped. There has been no recurrence of mania for almost 4 months.

Example 9

Patient swallowed two Norcos (1 Norco=10 mg hydrocodone+325 mg acetaminophen) 30 minutes prior to taking ¼ of an 8 mg tablet of Suboxone sublingually. He took the ¼ of an 8 mg tablet of Suboxone sublingually 3 times in day without experiencing any precipitated withdrawal. Norco is a short-acting narcotic; he was taking around 40-50 mg of Norco/day.

Example 10

This patient was taking 100 mg of long-acting morphine (Kadian) twice a day and 30 mg of short-acting oxycodone (Roxicodone) 5 times a day. He had just taken 1 Kadian and 2 Roxicodones 45 minutes prior to taking ¼ of an 8 mg tablet of Suboxone sublingually but experienced no withdrawal symptoms. He took ¼ of an 8 mg tablet of Suboxone tablet sublingually 6 more times that day without experiencing any withdrawal symptoms.

Example 11

This patient who had been previously placed on Suboxone had relapsed and was receiving about 40 mg of Methadone from "the street." She was restarted on ¼ of an 8 mg tablet of Suboxone taken twice a day and did not experience any withdrawal symptoms in spite of having taken her last dose of Methadone about 6 hours earlier.

Example 12

Seven patients diagnosed with bipolar II disorder and cyclothymia were determined to have initial GAF (global assessment of functioning) scores ranging from 31 to 60. Upon administration of Suboxone 8.0 mg twice a day and Geodon 40 mg once daily all seven patients experienced mood stabilization for three months or longer and an increase in GAF scores over 80. Specifically, administration of this medication regimen has resulted in mood stabilization for 12 months and an increase in GAF score from 31-40 to 81-90 (patient 1), mood stabilization for 7 months and an increase in GAF score from 51-60 to 81-90 (patient 2), mood stabilization for six months and an increase in GAF score from 51-60 to 81-90 (patient 3), an increase in GAF score from 31-40 to 81-90 (patients 4 and 5), mood stabilization for 17 months and an increase in GAF score from 11-20 to 81-90 (patient 6), and mood stabilization for four months and an increase in GAF score from 11-20 to 81-90.

Example 13

A patient diagnosed with mixed bipolar II disorder (depression and mania characterized by anxiety, impulsiveness, grandiosity, and pressured speech) and opioid-induced hypogonadism was initially determined to have a GAF score between 21-30. The patient was started on Suboxone 16 mg/day and Seroquel 100 mg/day. After three months of treatment, the patient remained highly anxious, and had intermittent manic episodes although he is no longer depressed.

Example 14

A patient diagnosed with mixed bipolar I disorder was determined to have a GAF score between 11-20. The patient was extremely depressed and manic simultaneously, with irritability, grandiosity, pressured speech, agitation, and impulsiveness coexisting with negative thoughts, guilty feelings, distractibility and suicidal ideation. She was in pain all the time, and barely able to get out of bed. She was also dependent on multiple narcotics. After treatment with 32 mg of Suboxone (8 mg four times a day) and 40 mg of Geodon, her GAF score improved to between 41-50. She also had more energy and less pain and was now able to get out of bed, but still felt highly anxious and manic for three months. Two months after increasing her Geodon to 120 mg, she is still stable and compliant with a GAF score between 71-80.

Example 15

A patient diagnosed with mixed bipolar I disorder (ultra rapid cycling) was initially determined to have a GAF score of between 0-10, and was addicted to multiple narcotics. She was also suicidal and completely non-functional with rapidly alternating mood swings multiple times in a day. She always complained of fibromyalgia pain. Her psychiatrist was giving her Seroquel but that had elevated her blood sugar. Since starting Suboxone 32 mg/day and Geodon 120 mg/day and stopping Seroquel, her GAF score improved to 71-80, and has been maintained at this level for one year. The patient is able to get out of bed, has less pain, and her diabetes mellitus is better controlled.

Example 16

A patient diagnosed with bipolar I disorder was initially determined to have a GAF score of 1-10. He was very depressed, in pain all the time both from the neuropathy and the fibromyalgia, and had attempted to overdose on two occasions. His psychiatrist had placed him on three antidepressants (Prozac, Elavil and Remeron) and 90 mg/day of Valium. After treatment with Suboxone 32 mg/day, Geodon 120 mg/day, Seroquel 25 mg/day, Remeron 30 mg/day, and Valium 30 mg/day, his GAF score was consistently in the range of 71-80 for the past seven months. The Prozac, Elavil, and Remeron are being stopped, and he has decreased his Valium from 90 mg/day to 30 mg/day. He is no longer depressed but complains of anxiety and neuropathic pain. The plan is to discharge the Seroquel if possible and start an anti-epileptic both for the neuropathic pain and control of the bipolar disease.

Example 17

A patient diagnosed with bipolar I disorder was initially determined to have a GAF score of 11-20. After treatment with Suboxone 8 mg four times a day (32 mg total), and Seroquel 300 mg/day, the patient's GAF score has been consistently between 81-90 for 18 months.

Example 18

A patient diagnosed with mixed bipolar I disorder was initially determined to have a GAF score of 21-30. She went to work everyday but suffered from extreme depression alternating with manic periods characterized by financial profligacy, grandiosity and insomnia with racing thoughts. Her course was worsened by drug and alcohol addiction. She was started on 24 mg of Suboxone and 400 mg of Seroquel and became manic. The Suboxone was decreased to 16 mg and now she is stable with a GAF between 81-90 for the past two months. However, she complains of excessive sedation in the AM because of Seroquel, so the dose will probably have to be lowered to 200 mg.

Example 19

This bipolar II patient presented for Suboxone maintenance. He was already taking Suboxone 8 mg twice a day, and his GAF score was 61-70. However, he suffered from extreme fatigue secondary to sleep apnea and opioid-induced low testosterone. Subsequently he was referred to a sleep clinic, started on CPAP, prescribed Seroquel 25 mg and testosterone replacement. This patient is now doing wonderfully well with a GAF greater than 90 over the past four months.

Example 20

A patient diagnosed with bipolar I disorder was initially determined to have a GAF score of 31-40. After administering Suboxone 8 mg twice a day for four months, his GAF score improved to 61-70. However, he still complained of depression. After addition of Seroquel 50 mg/day, his GAF score has improved to 81-90 for four months.

Example 21

This high functioning patient diagnosed with bipolar II disorder was initially determined to have a GAF score of greater than 70. She was taking Suboxone 8 mg twice a day, which was her maintenance dose. However, she began to show signs of hypomania—excessive talking, distraction, racing thoughts and insomnia. Thus, lithium 600 mg/day was added but the patient complained of side effects including tremulousness and stomach discomfort along with diarrhea. On her own the patient decreased the lithium dose to 300 mg and reported improvement in side effects. It is not clear whether she consistently takes the lithium, having consistently failed to get her blood levels checked. Nevertheless, she is stable and calmer with a GAF score of 80 for over a year.

Example 22

This patient diagnosed with bipolar I disorder was initially determined to have a GAF score of GAF of 21-30. He was addicted to hydrocodone, and very depressed. He managed to hold on to a job but his attendance was sporadic because he did not have the energy to report to work. After starting Zyprexa 5 mg/day and Suboxone 8 mg twice a day, his GAF score increased to 71-80, and he has consistently gone to work for one month. The plan going forward will also be to treat his sleep apnea and hypogonadism.

Example 23

This was a patient with mixed bipolar I features in which symptoms of severe depression and mania existed simultaneously. She was a poorly functioning patient with a GAF score between 0-10. She consistently complained of severe fibromyalgia-type pain, was addicted to high doses of morphine and repeatedly stated without expressing a specific plan to end her life and that she would be better off dead. Her GAF score has now been 51-60 for three months after starting Suboxone 8 mg four times a day, and Seroquel 200 mg/day, and Zyprexa 5 mg/day. She is better able to function and o longer expresses vague suicidal ideation. Conversations are more coherent because manic symptoms have abated and she is no longer hypervoluble. The plan going forward is to treat her sleep apnea with CPAP.

Example 24

A patient diagnosed with mixed bipolar I disorder was initially determined to have a GAF score of 31-40. This patient managed to hold down a job in spite of an addiction to painkillers and symptoms which included fatigue, irritability, grandiosity, impulsivity, distractibility, hopelessness, helpless and feelings of guilt and worthlessness. At 16 mg of Suboxone he improved to a GAF score of 41-50 for two months. While his manic symptoms disappeared, he was still very depressed. The Suboxone was increased to 32 mg and the patient reported that his depression diminished but he felt highly anxious. His GAF score was still in the range of 41-50. Mood stabilizers were then started (Seroquel 400 mg/day), and the Suboxone dose was decreased to 24 mg. He now has been functioning at a GAF score of 71-80 for four months. His major complaint is extreme exhaustion which may be attributable to his sleep apnea and hypogonadism which need to be addressed going forward.

Example 25

This bipolar I patient (rapid cycling) was initially determined to have a GAF score of 1-10 and extreme manic behavior. With Suboxone alone (2 mg/day), GAF score improved to 61-70. With Zyprexa 2.5 mg/day, GAF score improved to 71-80. The patient has been stable and compliant for three months.

Example 26

This mixed bipolar I patient was compliant and stable with a GAF score of around 80 for four months. The treatment regimen included Suboxone 8 mg twice a day and an antiepileptic (Lamictal 200 mg/day), which helped the bipolar symptoms and the pain from fibromyalgia. Due to financial constraints the patient could no longer afford Suboxone.

Example 27

This bipolar II patient's presentation was marked by excessive fatigue. She was unable to stay awake during the day and had difficulty sleeping at night. She was ruled out for any other causes of fatigue including anemia, underlying infection, narcolepsy, and sleep apnea. Her GAF score was initially 41-50. She was taking Methadone and Ritalin and was stable and compliant but exhausted and denied depression. Antidepressants did not seem to help. After starting on Suboxone 8 mg twice a day her GAF improved to 51-60. She reported a little more energy but not much. After 2 months on Risperdal 4 mg/day and Suboxone 8 mg twice a day, she has stopped Adderall, and her fatigue has virtually disappeared and her demeanor is very bright and animated. Her GAF score had been 81-90 now for two months.

Example 28

This was an extremely dysfunctional schizoaffective patient, disheveled, addicted to narcotics and benzodiazepines, unable to hold down a job, with disorganized schizophrenic symptoms consisting of bizarre and unpredictable behaviors, and inability to hold a conversation. GAF score has been 71-80 for two months since starting on Suboxone 24 mg and Trilafon 8 mg three times a day.

Example 29

A patient diagnosed with mixed bipolar I disorder was initially determined to have a GAF score of 11-20. With 16 mg of Suboxone and 5 mg of Zyprexa, the patient had an improved GAF score of 51-60, but was still depressed and experienced episodes of mania. Last month he was increased to Suboxone 24 mg/day. His GAF score is currently 61-70.

Example 30

This was a high functioning mixed bipolar II patient who presented with coexistent dysthymia and insomnia, fatigue with racing thoughts, and irritability in the context of drug addiction. The patient is now stable and compliant with a GAF score greater than 90 for over six months on a regimen of Suboxone 8 mg twice a day and Neurontin 1800 mg/day.

Example 31

A patient diagnosed with mixed bipolar II disorder had an initial GAF score of 61-70 with dysthymia, and extreme fatigue and insomnia with racing thoughts. After starting Suboxone 8 mg twice a day and Lyrica 50 mg/day, the patient's GAF score has increased to 81-90, and has remained stable at this level for 9 months.

Example 32

A patient diagnosed with mixed bipolar I disorder had an initial GAF score of 11-20. The patient was simultaneously depressed and manic with an inability to sleep because of racing thoughts and an inability to cope with any stressful situation. On 4 mg/day of Suboxone for 18 months, her GAF score was 31-40. She complained of extreme anxiety towards the evening. Now she is taking Suboxone 4 mg twice a day, and her GAF score has increased to over 80 for one month.

Example 33

A patient diagnosed with mixed bipolar I disorder had an initial GAF score of 0-10, and had two previous suicide attempts. Since starting Suboxone 32 mg/day and Geodon 160 mg/day, her GAF has improved to 31-40 for 6 months. She is still depressed but the depression is no longer catatonic and she no longer has suicidal thoughts. She was subsequently started on Zyprexa 5 mg/day and her GAF improved to 75 for three months. The plan going forward is to treat the sleep apnea.

Example 34

This mixed bipolar I patient had a GAF score of 21-30 while taking Suboxone 16 mg/day. The patient suffered from anorexia, and also displayed both manic and depressive symptoms. After starting Seroquel 100 mg/day, the patient's GAF score has now been 71-80 for 13 months. The patient has also gained 8 lbs.

Example 35

This patient with rapidly cycling bipolar disorder initially presented with a GAF score of 11-20. The GAF score has been 61-70 for two months after starting Suboxone 24 mg/day and Geodon 20 mg/day.

Example 36

This patient with rapidly cycling bipolar disorder initially presented with a GAF score of 31-40. The GAF score has been 81-90 for three months after starting Suboxone 24 mg/day and Zyprexa 5 mg/day.

Example 37

This patient with rapidly cycling bipolar disorder initially presented with a GAF score of 31-40. The GAF score has been 71-80 for six months after starting Suboxone 24 mg/day and Geodon 40 mg/day.

Example 38

A patient with bipolar II disorder (depression predominant), had an initial GAF score of 51-60. The GAF score is now 71-80 with Suboxone 24 mg/day and Seroquel 200 mg/day.

Example 39

This patient with bipolar I disorder had a GAF score of 11-21, and was manic appearing. The patient was already on Suboxone 24 mg/day, Lamictal 300 mg/day, Gabapentin, Trazadone, and Geodon 200 mg/day. The Trazadone (antidepressant) was discontinued and in its place Seroquel 200 mg/day and Zypexa 80 mg/day were started. Now the patient's mood is stabilized and GAF score is 41-50.

Example 40

A patient with rapidly cycling bipolar disorder had an initial GAF score of 11-20. Upon taking Suboxone 16 mg/day for six months, their GAF score improved to 51-60 but episodes of hypomania interspersed with depression still occurred. The Suboxone was increased to 32 mg/day. GAF score has subsequently increased to 81-90 now for 6 months.

Example 41

This patient with mixed bipolar I disorder had an initial GAF score of 21-30. For three months on Seroquel 100 mg/day and Suboxone 16 mg/day, the patient's GAF score improved to 61-70, but mixed episodes were still occurring. Geodon 40 mg/day was then started, and the patient's GAF score improved to 71-80, which has now been stable for 7 months.

Example 42

This patient with mixed bipolar I disorder had an initial GAF score of 21-30 and a history of crack cocaine addiction. His major complaint was difficulty sleeping due to racing thoughts. Geodon 80 mg/day and Suboxone 8 mg/day were started, but initially he could not tolerate the Geodon because it made him feel like he was "crawling out of his skin." He was started on an antihistamine (Benadryl 1×/day) for akisthisia and reported significant improvement. His GAF score is now 81-90, and has been stable for five months.

The invention claimed is:

1. A method for treating a manic episode in a subject suffering from a bipolar disorder or a subtype thereof, comprising administering buprenorphine or a pharmaceutically acceptable salt thereof to the subject to treat the manic episode.

2. The method of claim 1, wherein the bipolar disorder is bipolar I disorder.

3. The method of claim 1, wherein the bipolar disorder is bipolar II disorder.

4. The method of claim 1, wherein the bipolar disorder is mixed bipolar disorder.

5. The method of claim 4, wherein the subject affected with the mixed bipolar disorder rapidly cycles between manic or hypomanic phases and depressive phases.

6. The method of claim 5, wherein at least one episode of racing thoughts occurs during the depressive phase.

7. The method of claim 1, wherein the bipolar disorder subtype is cyclothymia.

8. The method of claim 1, wherein the bipolar disorder subtype is acute mania.

9. The method of claim 1, further comprising administering an opioid antagonist.

10. The method of claim 9, wherein the opioid antagonist comprises naloxone.

11. The method of claim 10, wherein buprenorphine and naloxone are administered together in a unit dose.

12. The method of claim 11, wherein about 2.0 mg of buprenorphine is administered in the unit dose.

13. The method of claim 11, wherein about 8.0 mg of buprenorphine is administered in the unit dose.

14. The method of claim 1, wherein about 2.0 mg of buprenorphine is administered to the subject.

15. The method of claim 1, wherein about 8.0 mg of buprenorphine is administered to the subject.

16. The method of claim 1, wherein a feature of the manic episode is that the subject experiences racing thoughts.

* * * * *